(12) United States Patent
Hansen et al.

(10) Patent No.: US 6,753,350 B1
(45) Date of Patent: Jun. 22, 2004

(54) METHOD TO REDUCE THE INCIDENCE OF INTRAVENTRICULAR HEMORRHAGE IN PRETERM INFANTS

(75) Inventors: James W. Hansen, Evansville, IN (US); Karen H. Knauff, Newburgh, IN (US); Deborah A. Schade, Evansville, IN (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/395,356

(22) Filed: Mar. 24, 2003

(51) Int. Cl.[7] .............................................. A61K 31/20

(52) U.S. Cl. ..................................................... 514/560

(58) Field of Search ................................. 514/549, 560

(56) References Cited

U.S. PATENT DOCUMENTS

| | | | | |
|---|---|---|---|---|
| 5,709,888 | A | * 1/1998 | Gil et al. ..................... | 424/522 |
| 6,180,671 | B1 | 1/2001 | Freedman et al. .......... | 514/560 |
| 6,342,530 | B1 | 1/2002 | Darko ......................... | 514/561 |
| 6,495,599 | B2 | 12/2002 | Auestad et al. ............. | 514/560 |
| 2002/0004527 | A1 | * 1/2002 | Auestad et al. ............. | 514/560 |
| 2002/0137796 | A1 | * 9/2002 | Schade et al. ............... | 514/558 |

OTHER PUBLICATIONS

Article published online on Preemie–L website posted Mar. 12, 1996, by Doug Derleth entitled Head Ultrasounds at http://home.vicnet.net.au/~garyh/arcmarch/0124.html, Mar. 16, 2002.
Review by Andrew Whitelaw edited Nov. 27, 2000, entitled intraventricular Streptokinase after intraventricular Hemorrhage in Newborn Infants at http://www.nichd.nih.gov/cochrane/Whitela2/Whitelaw.htm, Mar. 16, 2002.
Article published online on Neonatology on the Web by Asha Puri entitled Teaching Files: IVH/PVH Management and Prophylaxis at www.neonatology.org/syllabus/ivh.management.html, Mar. 16, 2002.
Article published online on E Medicine website by David J. Annibale et al. entitled Periventricular Hemorrhage–Intraventricular Hemorrhage at http://www.emedicine.com/ped/topic2595.htm, Mar. 16, 2002.
Article published in Canadian Family Physician vol. 46: 1233–1400 and published online on Canadian Family Physician website entitled Motherisk Update: Phenobarbital to Prevent Intraventricular Hemorrhage in Preterm Infants? at http://www.cfpc.ca/archive/communic/cfp/2000/06/04_01.htm, Mar. 16, 2002.
Patient Information from Vanderbilt Children's Hospital, The Learning Center, HC–0383 (9/97), entitled Intraventricular Hemorrhage (Infant).
Article published in The Journal of Pediatrics, Aug. 1992, vol. 121, No. 2, pp. 280–285 by Betty Vohr et al. entitled Effects of Intraventricular Hemorrhage and Socioeconomic Status on Perceptual, Cognitive, and Neurologic Status of Low Birth Weight Infants at 5 Years of Age.
Article published online on University of Wisconsin Children's Hospital website entitled For Parents of Preemies: Intraventricular Hemorrhage at http://www2.medsch.wisc.edu/childrenshosp/parents of preemies/ivh.html, Mar. 16, 2002.
Article published online on University of Minnesota Department of Pediatrics website entitled Intraventricular Hemorrhage at http://www.peds.umn.edu/divisions/neonatology/ivh.html, Mar. 16, 2002.
Abstract published online of Review published in The Cochrane Library, Issue 1, 2002, by A. Whitelaw entitled Postnatal Phenobarbitone for the Prevention of Intraventricular Hemorrhage in Preterm Infants (Cochrane Review) at http://www.update–software.com/ccweb/cochrane/revabstr/ab001691.htm, Mar. 16, 2002.
Article posted online by Michael J. Verive entitled Intraventricular Hemorrhage (IVH) at http://www.mverive.com/ivh.htm, Mar. 16, 2002.
Article published online on National Institute of Neurological Disorders and Stroke website, published in Apr. 1994 issue of Pediatrics, entitled Treatment Reduces Brain Hemorrhages in Very Low Birthweight Babies, Mar. 16, 2002.
Article published online on Emory University Division of Neonatal–Perinatal Medicine website by Neal P. Simon entitled Periventricular/Intraventricular Hemorrhage (PVH/IVH) in the Premature Infant at http://www.emory.edu/PEDS/NEONATOLOGY/DCP/pvhivh.htm, Mar. 16, 2002.
Article published online on St. John's Health Center website by Patricia Bromberger entitled Intraventricular Hemorrhage (IVH) of the Newborn at http://www.stjohns.org/HTL/NewBaby/22909.htm, Mar. 16, 2002.
Article published online on Kids Eat Great website by Christine Wood entitled Special Report: Prenatal Nutrition at http://www.kidseatgreat.com/prenatal.html, Mar. 18, 2002.
Brochure from Children's Hospitals and Clinics entitled Patient/Family Education: Intraventricular Hemorrhage (in Premature Babies), no date available.
Image of intraventricular hemorrhage (IVH) posted online on University of Utah Health Sciences Library website at http://medlib.med.utah.edu/WebPath/CNSHTML/CNS018.html, Mar. 16, 2002.
Article published online on Children's Medical Center of Dallas website entitled Intraventricular Hemorrhage at http://www.childrens.com/healthinfo/Display.cfm?ID=912&main=894, Mar. 16, 2002.

(List continued on next page.)

*Primary Examiner*—Raymond J. Henley, III
(74) *Attorney, Agent, or Firm*—Nelson Mullins Riley & Scarborough, LLP

(57) ABSTRACT

A method for reducing the incidence of Intraventricular Hemorrhage in preterm infants, involving the administration to those infants of a combination of docosahexaenoic acid and arachidonic acid.

29 Claims, No Drawings

OTHER PUBLICATIONS

Article published online on Lucile Packard Children's Hospital website entitled Neurological Disorders: Intraventricular Hemorrhage at http://www.lpch.org/HealthLibrary/ChildrensHealthAZ/neuro/ivh.htm, Mar. 16, 2002.

Abstract of article by M. Gleisner, Otto von Guericke University Magdeburg, Clinic for General Pediatrics and Neonatology entitled Risk Factors of Intraventricular Hemorrhage in Premature Infants, no date available.

Article published online on C.S. Mott Children's Hospital website entitled Prophylactic Indomethacin Prevents Intraventricular Hemorrhage at http://www.med.umich.edu/pediatrics/ebm/cats/ivh.htm, Mar. 16, 2002.

Abstract of article published in British Medical Journal, Jan. 3, 1998, vol. 316, No. 7124, pp. 21–25 by A.C. Wilson et al. entitled Relation of Infant Diet to Childhood Health—Seven Year Follow Up of Cohort of Children in Dundee Infant Feeding Study. Abstracts online at http://ovidweb.musc.edu/ovidweb.cgi, Mar. 17, 2003.

Abstract of article published in Pediatric Research, Oct. 1996, vol. 40, No. 4, pp. 627–632 by L. Taittonen et al. entitled Prenatal and Postnatal Factors in Predicting Later Blood Pressure Among Children—Cardiovascular Risk in Young Finns. Abstract online at http://ovidweb.musc.edu/ovidweb.cgi, Mar. 17, 2003.

Abstract of article published in Prostaglandins Leukotrienes & Essential Fatty Acids, Jul. 2002, vol. 67, No. 1, pp. 1–12 by U.N. Das entitled The Lipids that Matter from Infant Nutrition to Insulin Resistance. Abstract online at http://ovidweb.musc.edu/ovidweb.cgi, Mar. 17, 2003.

Abstract of article published in Pediatric Neurosurgery, 1997, vol. 26, No. 6, pp. 281–287 by R.J. Hudgins et al. entitled Intrathecal Urokinase as a Treatment for Intraventricular Hemorrhage in the Preterm Infant. Abstract online at http://www.karger.com/journals/PNE/PNE266/PNE0281.htm, Mar. 16, 2002.

Abstract of article published in Rev Mex Pediatr, 1997, vol. 64, No. 1, pp. 13–17 by J.M. Gonzalez–Ortiz et al. entitlted Factors Associated to Periventricular/Intraventricular Hemorrhage in Premature Infants Below 1,500 Grams of Weight. Abstract online at http://www.imbiomed.com.mx/SocPed/Spv64n1/english/Zsp71–03.html, Mar. 16, 2002.

Abstract of article published in Clin Neuropharmacol, Apr. 1987, vol. 10, No. 2, pp. 126–142 by J.M. Perlman and J.J. Volpe entitled Prevention of Neonatal Intraventricular Hemorrhage.

Brochure entitled Intraventrucular Hemorrhage (IVH) online at http://babyzone.com/drnathan/l/Intraventricular-hemorrhage.htm, Mar. 16, 2002.

Article submitted to the Massachusetts General Hospital Forum, Jul. 7, 1999, entitled Peroximal Disorders and DHA at http://neuro–www.mgh.harvard.edu/forum_2/ADHDF/7.7.999.31AMperoximaldiso.html, Mar. 18, 2002.

* cited by examiner

METHOD TO REDUCE THE INCIDENCE OF INTRAVENTRICULAR HEMORRHAGE IN PRETERM INFANTS

BACKGROUND OF THE INVENTION

1. Field of the Invention

The present invention relates generally to methods to reduce the incidence of Intraventricular Hemorrhage (IVH) in preterm infants. The present invention also relates to the supplementation with docosahexaenoic acid and arachidonic acid of infant formulas designed for preterm infants.

2. Description of Related Art

Intraventricular Hemorrhage (IVH), a bleeding from fragile blood vessels in the brain, is a significant cause of morbidity and mortality in premature infants and may have life-long neurological consequences such as cerebral palsy, mental retardation, and seizures. These vessels are especially fragile in preterm infants, particularly those born more than 8 weeks early, i.e., before 32 weeks of gestation. IVH is more commonly seen in extremely premature infants; its incidence is over 50% in preterm infants with birth weight less than 750 grams, and up to 25% in infants with birth weight less than 1000 to 1500 grams.

IVH encompasses a wide spectrum of intra-cranial vascular injuries with bleeding into the brain ventricles, a pair of C-shaped reservoirs, located in each half of the brain near its center, that contain cerebrospinal fluid. The bleeding occurs in the subependymal germinal matrix, a region of the developing brain located in close proximity to the ventricles. Within the germinal matrix, during fetal development, there is intense neuronal proliferation as neuroblasts divide and migrate into the cerebral parenchyma. This migration is about complete by about the $24^{th}$ week of gestation, although glial cells can still be found within the germinal matrix until term. The germinal matrix undergoes rapid involution from the $26^{th}$ to the $32^{nd}$ week of gestation, at which time regression is nearly complete, as glial precursors migrate out to populate the cerebral hemispheres.

Supporting this intense cell differentiation and proliferation activity there is a primitive and fragile capillary network. These vessels have thin walls for their relatively large size, lack a muscularis layer, have immature interendothelial junctions and basal laminae, and often lack direct contact with perivascular glial structures, suggesting diminished extravascular support. It is in this fragile capillary network where IVH originates. When a fetus is born prematurely, the infant is suddenly thrust from a well-controlled, protective environment into a stimulating, hostile one. Because of this physiologic stress and shock, the infant may lose the ability to regulate cerebral blood flow and may suffer alterations in blood flow and pressure and in the amounts of substances dissolved in the blood such as oxygen, glucose and sodium. The fragile capillaries may, and often do, rupture.

The severity of the condition depends on the extent of the vascular injury. There are four grades, or stages, of IVH as can be seen using ultrasound or brain computer tomography. Grade I IVH, the less severe stage, involves bleeding in the subependymal germinal matrix, with less than 10% involvement of the adjacent ventricles. Grade II IVH results when 10 to 40% of the ventricles are filled with blood, but without enlargement of the ventricles. Grade III IVH involves filling of over 50% of the ventricles with blood, with significant ventricular enlargement. In Grade IV IVH, the bleeding extends beyond the intraventricular area into the brain parenchyma (intraparenchymal hemorrhage).

The major complications of IVH relate to the destruction of the cerebral parenchyma and the development of posthemorrhagic hydrocephalus. Following parenchymal hemorrhages (Grade IV IVH), necrotic areas may form cysts that can become contiguous with the ventricles. Cerebral palsy is the primary neurological disorder observed in those cases, although mental retardation and seizures may also occur. In addition, infants affected with Grade III to IV IVH may develop posthemorrhagic hydrocephalus, a condition characterized by rapid growth of the lateral ventricles and excessive head growth within two weeks of the hemorrhage. Likely causes are obstruction of the cerebrospinal fluid conduits by blood clots or debris, impaired absorption of the cerebrospinal fluid at the arachnoid villi, or both. Another form of the hydrocephalus condition may develop weeks after the injury. In this case the likely cause is obstruction of the cerebrospinal fluid flow due to an obliterative arachnoiditis in the posterior fossa.

There is no specific treatment of IVH once it develops. Surgery will not prevent or cure the bleeding. Treatment of hydrocephalus may require use of spinal taps, ventricular reservoirs, or ventricular peritoneal shunts. A spinal tap is used to remove fluid from the spinal canal to reduce pressure. A needle is inserted in the infant's back to let fluid drip out. The procedure may allow time for the blood clots to clear by themselves and the fluid conduits to clear up. If the blockage is so severe that the fluid cannot circulate from the ventricles to the spinal canal, tubing can be surgically implanted into the ventricles (ventricular reservoirs). If the condition persists, a permanent tubing (shunt) can be placed in the ventricles. One end ot the tubing is placed in a ventricle, and the other is placed into the abdominal cavity. The tubing is tunneled under the skin.

Prevention of IVH is, thus, the favored approach. Prevention of prematurity, optimal management of labor and delivery, and the administration to mothers at risk of early delivery of drugs such as corticosteroids and phenobarbital are some of the methods of prenatal intervention aiming to reduce the incidence of IVH. Postnatal intervention on the premature infant is also possible. For example, indomethacin may be administered, a few hours after birth, to those premature infants that are at high risk of developing IVH. Indomethacin inhibits the formation of prostaglandins by decreasing the activity of the cyclooxygenase, may cause the maturation of the germinal matrix microvasculature, and is associated with decreased cerebral blood flow. Its use, however, is controversial as it may cause acute renal failure and other serious side effects.

Thus, there is a present need for a method to reduce the incidence of Intraventricular Hemorrhage in preterm infants. The method must not negatively affect growth pattern, must be safe to be administered to infants, and, if administered as part of the nutritional intake of the infants, this feeding must be well tolerated by the infants.

It is now known in the art that polyunsaturated fatty acids (PUFA) of both the n-3 and n-6 families are required for normal growth and development. See Innis, S. M. et al., Prog Lipid Res 1991; 30:39–103; see also Neuringer, M. and Conner, W. E. Nutr Rev 1986; 44:285–294. The n-3 long chain polyunsaturated fatty acid (LCPUFA), docosahexaenoic acid (DHA, 22:6n-3) is required for optimal brain, neural, and retinal development (See Innis et al. (1991), opus cit.; see also Neuringer and Connor (1986), opus cit.) and the n-6 LCPUFA arachidonic acid (ARA, 20:4n-6) is needed to support good growth and development (See Carlson, S. E. et al., Am J Clin Nutr 1993; 58:35–42). Infants who are breast-fed receive these LCPUFA in their diet because human milk contains low levels of DHA and ARA. While the amounts of DHA and ARA in human milk vary among individual women and populations depending upon maternal diets, studies across many population groups have shown the median levels of DHA and ARA in human milk to be approximately 0.3% and 0.5–0.6% of total fatty acid content, respectively. See Innis, S. M., J Pediatr 1992; 120:S56–61; see also Koletzko, B. et al., J Pediatr 1992; 120:S62–70.

Infant formulas currently marketed in the United States did not until recently contain any preformed DHA or ARA. Thus, infants solely fed these infant formulas ingest no DHA or ARA. The formulas do, however, contain the 18-carbon chain length essential fatty acids, alpha linolenic (linolenic) acid (ALA, 18:3n-3) and linoleic acid (LA, 18:2n-6), at levels equal to or greater than the levels present in most human milks (Innis 1992). Infants can synthesize the n-3 and n-6 LCPUFA, DHA and ARA, from these 18-carbon precursor fatty acids (linolenic and linoleic acid, respectively) by a series of metabolic steps requiring desaturation and elongation. See Carnielli, V. P. et al., Pediatr Res 1996; 40:169–174; see also Salem, N. et al., Proc Natl Acad Sci 1996; 93:49–54; see also Sauerwald, T. U. et al., Pediatr Res 1997; 41:183–187. It is not clear, however, whether all infants, especially preterm infants, are capable of synthesizing enough DHA and ARA from the precursors, linolenic and linoleic acids, to meet their growth and development needs.

Diersen-Schade et al. (in: Riemersma, R. et al. (editors), Essential Fatty Acids and Eicosanoids: Invited Papers from the Fourth International Congress, p. 123–7 (1998)) examined the safety and effects of feeding relatively healthy preterm infants, formulas supplemented with just DHA or DHA and ARA sourced from the single cell Martek oils, DHASCO® and ARASCO®, at the median levels found in human milk. See Koletzko et al. (1992), opus cit. That study was designed to feed relatively healthy preterm infants for at least twenty-eight days after the start of enteral feeds with one of three study formulas: a Control formula with no DHA or ARA, a formula supplemented with DHA, or a formula supplemented with DHA and ARA.

After twenty-eight days, the subjects were fed a commercial cow's milk based, routine formula. The subjects were followed up to 57 Weeks Postmenstrual Age (PMA). Results from that study were intriguing. Even though the preterm subjects had been fed the study formulas for only twenty-eight days, differences in weight gains and mean achieved weights were detected for the DHA+ARA supplemented group compared to the Control group. For the twenty-eight day study period during which the study formulas were ingested, subjects in the DHA+ARA supplemented group gained more weight than the subjects in the Control group. At 48 Weeks PMA, subjects in the group supplemented with DHA and ARA had a greater mean achieved weight than that for the Control group or the group supplemented with DHA only. The mean weight of the group supplemented with DHA and ARA was also not significantly different from that of a reference term infant group that had been exclusively fed with human milk. By 57 Weeks PMA, the mean weight of the group supplemented with DHA and ARA was no longer significantly different than the other two formula groups. This DHA and ARA supplemented group was, however, the only formula group with a mean weight not significantly less than that of the human milk fed term infants.

The Diersen-Schade et al. (1998), opus cit. study showed that the formula, supplemented with DHA and ARA at median levels found in human milk, had benefited the preterm infants with an earlier phase of catch-up growth even though the supplementation was administered for a short (twenty-eight days) period. The study raised the need for a long-term feeding study in premature infants to determine: 1) if such long-term feeding of these LCPUFA was safe, and 2) if the growth benefits would be even more enhanced by a longer feeding period.

In addition, the study should include infants who are not, "relatively healthy" to mirror preterms as they are found in actual clinical practice. This approach would mean a study population with multiple concomitant medical conditions related to prematurity. Because the study population would be less healthy than the preterm subjects in the Diersen-Schade et al. study, and because there is a concern among some nutritional scientists that formulas supplemented with DHA and ARA may increase the risk of the preterm infant for greater morbidity, the subjects would have to be tracked, especially in the early hospitalization period, for concomitant medical conditions common in the postnatal course of preterm infants, such as necrotizing enterocolitis (NEC), retinopathy of prematurity (ROP), sepsis, bronchopulmonary dysplasia (BPD), and intraventricular hemorrhage (IVH), with or without hydrocephalus. IVH would be of special significance as there is some concern that supplementation with long chain omega-3 PUFA might lead to increased bleeding or increased incidence or severity of IVH.

SUMMARY OF THE INVENTION

It has now been discovered through the present invention that the administration to very low birth weight (VLBW) premature infants of a combination of docosahexaenoic acid (DHA) and arachidonic acid (ARA) from a source that is substantially free of eicosapentaenoic acid (EPA) reduces the incidence of IVH in those infants and results in nonspecific low blood pressure readings in those infants. These surprising discoveries are a consequence of a study conducted to determine the effect of feeding DHA- and ARA-supplemented infant formulas to VLBW infants on the infants' growth.

In addition to discovering that supplementation of infant formulas with long chain omega-3 PUFA does not lead to increased bleeding (See Heird, W. C., Lipids 1999; 34:207–214) which could lead to increased incidence or severity of IVH, when the source of omega-3 PUFA is substantially free of EPA, the VLBW infants fed with the supplemented formula show a reduced incidence of IVH. Thus, the present invention surprisingly addresses the need for a method to reduce the incidence of Intraventricular Hemorrhage in preterm infants. The method does not negatively affect growth pattern, is safe to be administered to infants, and, if administered as part of the nutritional intake of the infants, this feeding is well tolerated by the infants.

The present invention is directed to a novel method to reduce the incidence of Intraventricular Hemorrhage in preterm infants. This novel method comprises administering the infants with an effective amount of docosahexaenoic acid and arachidonic acid substantially free of eicosapentaenoic acid. The LCP fatty acids may be administered using a DHA- and ARA-supplemented formula. The formula does not negatively alter growth patterns, is well tolerated and imposes no safety issues.

DETAILED DESCRIPTION OF THE INVENTION

The present invention relates to a method of reducing the incidence of Intraventricular Hemorrhage in preterm infants.

The method comprises administering to those infants a combination of DHA and ARA, substantially free of eicosapentaenoic acid (EPA).

In one embodiment of the invention, the combination of DHA and ARA is administered as part of an infant formula. The infant formula for use in the present invention is, typically, nutritionally complete and contains suitable types and amounts of lipids, carbohydrates, proteins, vitamins and minerals. The amount of lipids or fats typically can vary from about 3 to about 7 g/100 kcal. The amount of proteins typically can vary from about 1 to about 5 g/100 kcal. The amount of carbohydrates typically can vary from about 8 to about 14 g/100 kcal. Protein sources can be any used in the art, e.g., nonfat milk, whey protein, casein, soy protein, hydrolyzed protein, and amino acids. Lipid sources can be any used in the art, e.g., vegetable oils such as palm oil, soybean oil, palm olein oil, coconut oil, corn oil, canola oil, low erucic acid rapeseed oil, sunflower oil, safflower oil, medium chain triglyceride oils, high oleic sunflower oil, and high oleic safflower oil. Carbohydrate sources can be any known in the art, e.g., lactose, glucose polymers, corn syrup solids, maltodextrins, sucrose, starch, and rice syrup solids. Conveniently, several commercially available infant formulas can be used. For example, Enfamil® Premature Formula, EnfaCare®, and Enfamil® With Iron (all available from Mead Johnson & Company, Evansville, Ind., U.S.A.) may be supplemented with suitable levels of ARA and DHA at the proper ratios and used to practice the method of the present invention. Particular infant formulas suitable for use in the present invention are described in the Example.

The form of administration of DHA and ARA in the method of the present invention is not critical, as long as an effective amount is administered. Most conveniently, DHA and ARA are supplemented into an infant formula to be fed to the infants after the infants receive their first enteral feeding. Alternatively, DHA and ARA can be administered as a supplement not integral to formula feeding, for example, as oil drops, sachets or in combination with other nutrients such as vitamins.

The method of the invention requires a combination of DHA and ARA. The weight ratio of ARA:DHA is typically from about 1:3 to about 9:1. In one embodiment of the present invention, this ratio is from about 1:2 to about 4:1. In yet another embodiment, the ratio is from about 2:3 to about 2:1. In one particular embodiment the ratio is about 2:1.

The effective amount of DHA for use in the present invention is typically from about 3 mg per kg of body weight per day to about 150 mg per kg of body weight per day. In one embodiment of the invention, the amount is from about 6 mg per kg of body weight per day to about 100 mg per kg of body weight per day. In another embodiment the amount is from about 10 mg per kg of body weight per day to about 60 mg per kg of body weight per day. In yet another embodiment the amount is from about 15 mg per kg of body weight per day to about 30 mg per kg of body weight per day.

The effective amount of ARA for use in the present invention is typically from about 5 mg per kg of body weight per day to about 150 mg per kg of body weight per day. In one embodiment of this invention, the amount varies from about 10 mg per kg of body weight per day to about 120 mg per kg of body weight per day. In another embodiment, the amount varies from about 15 mg per kg of body weight per day to about 90 mg per kg of body weight per day. In yet another embodiment, the amount varies from about 20 mg per kg of body weight per day to about 60 mg per kg of body weight per day.

The amount of DHA in infant formulas for use in the present invention typically varies from about 5 mg/100 kcal to about 80 mg/100 kcal. In one embodiment of the present invention it varies from about 10 mg/100 kcal to about 50 mg/100 kcal; and in another embodiment from about 15 mg/100 kcal to about 20 mg/100 kcal. In a particular embodiment of the present invention, the amount of DHA is about 17 mg/100 kcal.

The amount of ARA in infant formulas for use in the present invention typically varies from about 10 mg/100 kcal to about 100 mg/100 kcal. In one embodiment of the present invention, the amount of ARA varies from about 15 mg/100 kcal to about 70 mg/100 kcal. In another embodiment the amount of ARA varies from about 20 mg/100 kcal to about 40 mg/100 kcal. In a particular embodiment of the present invention, the amount of ARA is about 34 mg/100 kcal.

The infant formula supplemented with oils containing DHA and ARA for use in the present invention can be made using standard techniques known in the art. For example, they can be added to the formula by replacing an equivalent amount of an oil, such as high oleic sunflower oil, normally present in the formula. As another example, the oils containing DHA and ARA can be added to the formula by replacing an equivalent amount of the rest of the overall fat blend normally present in the formula without DHA and ARA.

The source of DHA and ARA can be any source known in the art as long as it is substantially free of EPA. In one embodiment of the present invention, sources of DHA and ARA are single cell oils as taught in U.S. Pat. Nos. 5,374,567; 5,550,156; and 5,397,591, the disclosures of which are incorporated herein in their entirety by reference. However, the present invention is not limited to only such oils. DHA and ARA can be in natural form provided that the remainder of the LCP source is substantially free of EPA and does not result in a deleterious effect on the infant. Alternatively, DHA and ARA can be used in refined form. The LCP source used in the present invention is substantially free of EPA. For example, in one embodiment of the present invention the infant formula contains less than about 16 mg EPA/100 kcal; in another embodiment less than about 10 mg EPA/100 kcal; and in yet another embodiment less than about 5 mg EPA/100 kcal. One particular embodiment contains substantially no EPA. Another embodiment is free of EPA in that even trace amounts of EPA are absent from the formula.

EXAMPLE

This example illustrates the effect of feeding infant formulas supplemented with a combination of DHA and ARA that is substantially free of EPA to VLBW preterm infants (<1500 g birth weight) on the incidence of IVH. The example is part of a larger study conducted to determine the effects of long-term feeding of preterm infants with DHA- and ARA-supplemented formulas on the infants' growth and development. Only those aspects relating to the effect of such feedings on IVH incidence are shown in detail here.

Rationale for the Study

The study is a continuation and expansion of Diersen-Schade, et al.'s earlier clinical study that examined the safety and tolerance of feeding relatively healthy preterm subjects for approximately the first 28 days of enteral feeding with an unsupplemented preterm formula [C] or a preterm formula supplemented with just DHA [D] or DHA and ARA [DA] sourced from the Martek single cell oils, DHASCO® and ARASCO®, at the median levels found in human milk. Infants were then fed a routine cow's milk formula to 57 Weeks Postmenstrual Age (PMA) or approximately four months corrected age. That study showed that subjects fed D and DA gained more weight in the 28-day study formula period than did those fed C with the difference between DA and C being statistically significant. At 48 Weeks PMA, DA subjects had a greater mean achieved weight than C or D subjects; at 57 Weeks PMA, there were no differences among the study formula groups in mean achieved weight. At 48 and 57 Weeks PMA, Group C and Group D, but not group DA had mean achieved weights significantly less than that of a reference group of breast-fed term infants. It appeared that the relatively short 28-day period of feeding the formula supplemented with DHA and ARA had provided the preterm subjects with an early period of "catch-up" growth, allowing them to be more like their term peers. There were no differences among the study formula groups in regards to serious adverse events or clinical complications.

Given the positive growth benefits that occurred with the short feeding period, a follow-up study was designed to investigate benefits that might occur if the supplemented formula were fed for longer periods of time (up to 57 Weeks PMA as the sole source of nutrition and up to 92 Weeks PMA as the sole infant formula used). The new study was also designed to include as wide a range of preterm infants as possible by enrolling preterm subjects as they appear in clinical practice, not just "relatively healthy" preterm infants. Safety, including the occurrence of concomitant medical conditions, adverse events, and laboratory results, and growth were the main parameters of interest but the investigation also included evaluation of any effects of the LCPUFA supplemented formulas on visual acuity, and on long-term mental and psychomotor development.

Summary of Study Objectives

The main purpose of the study was to evaluate the effects of long-term feeding of infant formulas supplemented with DHA and ARA to VLBW preterm infants (<1500 g birth weight) on the infants' growth, as a surrogate measure of safety, and development. The primary objective was to compare the mean achieved weights of preterm infants who ingested a Control formula or one of two supplemented formulas from enrollment to 92 Weeks PMA and to compare the mean achieved weights of the three formula groups at 92 Weeks PMA.

Secondary objectives were to determine: (1) the effect of feeding the study formulas on the mental and motor development of the preterm infants at 118 Weeks PMA by use of the Bayley Scales of Infant Development II; (2) the effect of that feeding on visual acuity using visual evoked potential (VEP) testing and random dot stereoacuity testing; and (3) the safety of feeding the supplemented formulas to preterm infants by assessing the incidence of adverse events, medical conditions specific to the early postnatal period, laboratory test results significantly different from the Control subjects, and discontinuations from the study for product-related or non-product-related reasons.

The age of the preterm subjects is expressed as Weeks PMA, where PMA stands for postmenstrual age. This terminology was chosen rather than postconceptional age because it is a more accurate reflection of gestational age. The gestational age of an infant is based on the number of weeks since the first day of the last menstrual period (LMP) of the mother, not on the number of weeks since conception. The standard "40 weeks term gestation" is based on 40 weeks since the LMP; the actual length of gestation from conception averages two weeks less than this or about 38 weeks.

Study Formulas

Infants were randomized to receive one of three milk-based study formulas: the Control formula (C), which did not contain DHA and ARA; the DAS formula which was identical to the Control formula except that it also contained 17 mg/100 kcal of DHA and 34 mg/100 kcal of ARA sourced from Martek's single cell oils, DHASCO® and ARASCO®; or the DAF formula that was identical to the Control formula except that it also included 17 mg/100 kcal of DHA sourced from a low EPA tuna fish oil (Roche 23% marine oil) and 34 mg/100 kcal of ARA sourced from Martek's single cell oil, ARASCO®. The amount of EPA in the Roche 23% marine oil is low (about 5.6%). When this oil is used in the DAF formula, the amount of EPA in the formula is in the range of that present in breast milk. See Koletzko et al. (1992), *opus cit.*

This study was designed to reflect the current clinical practices for feeding preterm infants from the first enteral feeds through 118 Weeks PMA. In clinical practice, preterm infants graduate according to their individual medical and nutritional needs from a preterm formula that has 24 kcal/30 mL to a discharge formula with 22 kcal/30 mL and eventually to a term formula with 20 kcal/30 mL. These types of formulas vary not only in caloric content but also in the levels of proteins, carbohydrates, fats, vitamins, and minerals to best suit the developing needs of the preterm infant. Some tiny preterm infants may ingest the preterm type of formula (24 kcal/30 mL) for many months, while others may go in a short period of time directly from the preterm formula to the term formula. Others may graduate to the discharge formula (22 kcal/30 mL) rather quickly, but then stay on the discharge formula for a long period of time.

It was anticipated that the study formula was to be the sole source of nutrition for study subjects from enrollment to 57 Weeks PMA unless the parents were otherwise instructed by their physician. After that time, solids and juices could be added to infant's diets. After 92 Weeks PMA, the study formulas were discontinued and parents were allowed to feed their infants regular milk or any formula of their choice. To accommodate the current clinical practice of feeding preterm, discharge, and term formulas to premature infants, according to their individual medical and nutritional needs; and to provide formulas that were appropriate to feed over such a long study period, each of the study formulas, Control, DAS, and DAF, was made available in the three types of infant formulas: preterm (24 kcal/30 mL), discharge (22 kcal/30 mL), and term (20 kcal/30 mL). These formulas correspond in nutrient composition to Enfamil® Premature Formula (EPF), EnfaCare®, and Enfamil® With Iron. In all cases, the amounts of DHA and ARA were kept constant across the study formula groups; i.e., there was no DHA or ARA in the Control premature study formula, the Control discharge study formula, or the Control term study formula. There was 17 mg/100 kcal of DHA and 34 mg/100 kcal of ARA, sourced from the Martek single cell oils DHASCO® and ARASCO®, respectively in the DAS preterm study formula, the DAS discharge study formula, and the DAS term study formula. There was 17 mg/100 kcal DHA sourced from Roche marine oil (tuna oil) and 34 mg/100 kcal ARA sourced from the Martek single cell oil, ARASCO®, in the DAF preterm study formula, the DAF discharge study formula, and the DAF term study formula. Tables 1–3 provide the nutritional composition of the three study formulas (Control, DAS, and DAF) for each type of formula: preterm, discharge, and term. In addition, for reference purposes, the final column of each table depicts the formulation of the currently marketed formula of that type, e.g., Enfamil® Premature Formula fortified with iron in Table 1, EnfaCare® formula in Table 2, and Enfamil® with Iron in Table 3, all available from Mead Johnson & Company, Evansville, Ind., U.S.A.

TABLE 1

Composition of Preterm Study Formulas (24 kcal/30 mL)

| Nutrients (per 100 kcal) | Study Group* | | | Marketed EPF** |
|---|---|---|---|---|
| | C | DAS | DAF | |
| Calories, kcal | 100.0 | 100.0 | 100.0 | 100.0 |
| Protein, g | 3.0 | 3.0 | 3.0 | 3.0 |
| Fat, g | 5.1 | 5.1 | 5.1 | 5.1 |
| Carbohydrate, g | 11.1 | 11.1 | 11.1 | 11.1 |
| Linoleic Acid, mg | 810.0 | 810.0 | 810.0 | 1060.0 |
| Linolenic Acid, mg | 110.0 | 110.0 | 110.0 | 152.0 |
| Docosahexaenoic Acid, mg | 0.0 | 17.0 | 17.0 | 0.0 |
| Arachidonic Acid, mg | 0.0 | 34.0 | 34.0 | 0.0 |
| Vitamin A, IU | 1250.0 | 1250.0 | 1250.0 | 1250.0 |
| Vitamin D, IU | 270.0 | 270.0 | 270.0 | 270.0 |
| Vitamin E, IU | 6.3 | 6.3 | 6.3 | 6.3 |
| Vitamin K, mcg | 8.0 | 8.0 | 8.0 | 8.0 |
| Thiamin, mcg | 200.0 | 200.0 | 200.0 | 200.0 |
| Riboflavin, mcg | 300.0 | 300.0 | 300.0 | 300.0 |
| Vitamin B6, mcg | 150.0 | 150.0 | 150.0 | 150.0 |
| Vitamin B12, mcg | 0.25 | 0.25 | 0.25 | 0.25 |
| Niacin, mcg | 4000.0 | 4000.0 | 4000.0 | 4000.0 |
| Folic Acid, mcg | 35.0 | 35.0 | 35.0 | 35.0 |
| Pantothenic Acid, mcg | 1200.0 | 1200.0 | 1200.0 | 1200.0 |
| Biotin, mcg | 4.0 | 4.0 | 4.0 | 4.0 |
| Vitamin C, mg | 20.0 | 20.0 | 20.0 | 20.0 |
| Choline, mg | 18.0 | 18.0 | 18.0 | 12.0 |
| Inositol, mg | 45.0 | 45.0 | 45.0 | 17.0 |
| Taurine, mg | 6.0 | 6.0 | 6.0 | 6.0 |
| Carnitine, m | 2.0 | 2.0 | 2.0 | 2.0 |
| Calcium, mg | 165.0 | 165.0 | 165.0 | 165.0 |
| Phosphorus, mg | 83.0 | 83.0 | 83.0 | 83.0 |
| Magnesium, mg | 6.8 | 6.8 | 6.8 | 6.8 |
| Iron, mg | 1.8 | 1.8 | 1.8 | 1.8 |
| Zinc, mg | 1.5 | 1.5 | 1.5 | 1.5 |
| Manganese, mcg | 6.3 | 6.3 | 6.3 | 6.3 |
| Copper, mcg | 120.0 | 120.0 | 120.0 | 125.0 |
| Iodine, mcg | 25.0 | 25.0 | 25.0 | 25.0 |
| Selenium, mcg | 1.8 | 1.8 | 1.8 | 1.8 |
| Sodium, mg | 40.0 | 40.0 | 40.0 | 39.0 |
| Potassium, mg | 100.0 | 100.0 | 100.0 | 103.0 |
| Chloride, mg | 85.0 | 85.0 | 85.0 | 85.0 |
| AMP Equivalents, mg | 0.60 | 0.60 | 0.60 | 0.03 |
| CMP Equivalents, mg | 1.29 | 1.29 | 1.29 | 0.59 |
| GMP Equivalents, mg | 0.61 | 0.61 | 0.61 | 0.11 |
| UMP Equivalents, mg | 0.71 | 0.71 | 0.71 | 0.61 |

Notes:
*C = Control formula without DHA or ARA; DAS = formula with DHA and ARA from single cell oils; DAF = formula with DHA from tuna fish oil and ARA from single cell oil.
**Iron-fortified Enfamil ® Premature Formula marketed at the time the study was conducted.

TABLE 2

Composition of Discharge Study Formulas (22 kcal/30 mL)

| Nutrients ((per 100 kcal) | Study Group | | | Marketed** EnfaCare ® |
|---|---|---|---|---|
| | C | DAS | DAF | |
| Calories, kcal | 100.0 | 100.0 | 100.0 | 100.0 |
| Protein, g | 2.8 | 2.8 | 2.8 | 2.8 |
| Fat, g | 5.3 | 5.3 | 5.3 | 5.3 |
| Carbohydrate, g | 10.4 | 10.4 | 10.4 | 10.7 |
| Linoleic Acid, mg | 900.0 | 900.0 | 900.0 | 950.0 |
| Linolenic Acid, mg | 115.0 | 115.0 | 115.0 | 115.0 |
| Docosahexaenoic Acid, mg | 0.0 | 17.0 | 17.0 | 0.0 |
| Arachidonic Acid, mg | 0.0 | 34.0 | 34.0 | 0.0 |
| Vitamin A, IU | 450.0 | 450.0 | 450.0 | 450.0 |
| Vitamin D, IU | 80.0 | 80.0 | 80.0 | 80.0 |
| Vitamin E, IU | 4.0 | 4.0 | 4.0 | 4.0 |
| Vitamin K, mcg | 8.0 | 8.0 | 8.0 | 8.0 |
| Thiamin, mcg | 200.0 | 200.0 | 200.0 | 200.0 |
| Riboflavin, mcg | 200.0 | 200.0 | 200.0 | 200.0 |
| Vitamin B6, mcg | 100.0 | 100.0 | 100.0 | 100.0 |
| Vitamin B12, mcg | 0.3 | 0.3 | 0.3 | 0.3 |
| Niacin, mcg | 2000.0 | 2000.0 | 2000.0 | 2000.0 |
| Folic Acid, mcg | 26.0 | 26.0 | 26.0 | 26.0 |
| Pantothenic Acid, mcg | 850.0 | 850.0 | 850.0 | 850.0 |
| Biotin, mcg | 6.0 | 6.0 | 6.0 | 6.0 |
| Vitamin C, mg | 16.0 | 16.0 | 16.0 | 16.0 |
| Choline, mg | 15.0 | 15.0 | 15.0 | 15.0 |
| Inositol, mg | 30.0 | 30.0 | 30.0 | 30.0 |
| Taurine, mg | 6.0 | 6.0 | 6.0 | 6.0 |
| Carnitine, mg | 2.0 | 2.0 | 2.0 | 2.0 |
| Calcium, mg | 120.0 | 120.0 | 120.0 | 120.0 |
| Phosphorus, mg | 66.0 | 66.0 | 66.0 | 66.0 |
| Magnesium, mg | 8.0 | 8.0 | 8.0 | 8.0 |
| Iron, mg | 1.8 | 1.8 | 1.8 | 1.8 |
| Zinc, mg | 1.25 | 1.25 | 1.25 | 1.25 |
| Manganese, mcg | 15.0 | 15.0 | 15.0 | 15.0 |
| Copper, mcg | 120.0 | 120.0 | 120.0 | 120.0 |
| Iodine, mcg | 15.0 | 15.0 | 15.0 | 15.0 |
| Selenium, mcg | 2.3 | 2.3 | 2.3 | 2.3 |
| Sodium, mg | 35.0 | 35.0 | 35.0 | 35.0 |
| Potassium, mg | 105.0 | 105.0 | 105.0 | 105.0 |
| Chloride, mg | 78.0 | 78.0 | 78.0 | 78.0 |
| AMP Equivalents, mg | 0.72 | 0.72 | 0.72 | 0.5 |
| CMP Equivalents, mg | 1.40 | 1.40 | 1.40 | 2.5 |
| GMP Equivalents, mg | 0.70 | 0.70 | 0.70 | 0.3 |
| UMP Equivalents, mg | 0.70 | 0.70 | 0.70 | 0.9 |

Notes:
*C = Control formula without DHA or ARA; DAS = formula with DHA and ARA from single cell oils; DAF = formula with DHA from tuna fish oil and ARA from single cell oil.
**EnfaCare ® formula marketed at the time the study was conducted.

TABLE 3

Composition of Term Study Formula (20 kcal/30 mL)

| Nutrients ((per 100 kcal) | Study Group* | | | Marketed** Enfamil ® with Iron |
|---|---|---|---|---|
| | C | DAS | DAF | |
| Calories, kcal | 100.0 | 100.0 | 100.0 | 100.0 |
| Protein, g | 2.1 | 2.1 | 2.1 | 2.1 |
| Fat, g | 5.3 | 5.3 | 5.3 | 5.3 |
| Carbohydrate, g | 10.9 | 10.9 | 10.9 | 10.9 |
| Linoleic Acid, mg | 860.0 | 860.0 | 860.0 | 860.0 |
| Linolenic Acid, mg | 85.0 | 85.0 | 85.0 | 85.0 |
| Docosahexaenoic Acid, mg | 0.0 | 17.0 | 17.0 | 0.0 |
| Arachidonic Acid, mg | 0.0 | 34.0 | 34.0 | 0.0 |
| Vitamin A, IU | 300.0 | 300.0 | 300.0 | 300.0 |
| Vitamin D, IU | 60.0 | 60.0 | 60.0 | 60.0 |
| Vitamin E, IU | 2.0 | 2.0 | 2.0 | 2.0 |
| Vitamin K, mcg | 8.0 | 8.0 | 8.0 | 8.0 |
| Thiamin, mcg | 80.0 | 80.0 | 80.0 | 80.0 |
| Riboflavin, mcg | 140.0 | 140.0 | 140.0 | 140.0 |
| Vitamin B6, mcg | 60.0 | 60.0 | 60.0 | 60.0 |
| Vitamin B12, mcg | 0.3 | 0.3 | 0.3 | 0.3 |
| Niacin, mcg | 1000.0 | 1000.0 | 1000.0 | 1000.0 |
| Folic Acid, mcg | 16.0 | 16.0 | 16.0 | 16.0 |
| Pantothenic Acid, mcg | 500.0 | 500.0 | 500.0 | 500.0 |
| Biotin, mcg | 3.0 | 3.0 | 3.0 | 3.0 |
| Vitamin C, mg | 12.0 | 12.0 | 12.0 | 12.0 |

TABLE 3-continued

Composition of Term Study Formula (20 kcal/30 mL)

| Nutrients ((per 100 kcal) | Study Group* | | | Marketed** Enfamil ® with Iron |
|---|---|---|---|---|
| | C | DAS | DAF | |
| Choline, mg | 12.0 | 12.0 | 12.0 | 12.0 |
| Inositol, mg | 6.0 | 6.0 | 6.0 | 6.0 |
| Taurine, mg | 6.0 | 6.0 | 6.0 | 6.0 |
| Carnitine, mg | 2.0 | 2.0 | 2.0 | 2.0 |
| Calcium, mg | 78.0 | 78.0 | 78.0 | 78.0 |
| Phosphorus, mg | 53.0 | 53.0 | 53.0 | 53.0 |
| Magnesium, mg | 8.0 | 8.0 | 8.0 | 8.0 |
| Iron, mg | 1.8 | 1.8 | 1.8 | 1.8 |
| Zinc, mg | 1.0 | 1.0 | 1.0 | 1.0 |
| Manganese, mcg | 15.0 | 15.0 | 15.0 | 15.0 |
| Copper, mcg | 75.0 | 75.0 | 75.0 | 75.0 |
| Iodine, mcg | 10.0 | 10.0 | 10.0 | 10.0 |
| Selenium, mcg | 2.8 | 2.8 | 2.8 | 2.8 |
| Sodium, mg | 27.0 | 27.0 | 27.0 | 27.0 |
| Potassium, mg | 108.0 | 108.0 | 108.0 | 108.0 |
| Chloride, mg | 63.0 | 63.0 | 63.0 | 63.0 |
| AMP Equivalents, mg | 0.74 | 0.74 | 0.74 | 0.5 |
| CMP Equivalents, mg | 1.63 | 1.63 | 1.63 | 2.5 |
| GMP Equivalents, mg | 0.59 | 0.59 | 0.59 | 0.3 |
| UMP Equivalents, mg | 0.89 | 0.89 | 0.89 | 0.9 |

Notes:
*C = Control formula without DHA or ARA; DAS = formula with DHA and ARA from single cell oils; DAF = formula with DHA from tuna fish oil and ARA from single cell oil.
**Enfamil ® with Iron marketed at the time the study was conducted.

The daily intake levels of DHA and ARA for any given subject were dependent upon whether they received the supplemented or unsupplemented formulas and the amount of formula they consumed. It is recommended that preterm infants consume between 110–150 kcal/kg/day of infant formula in the hospital; between 90–120 kcal/kg/day of infant formula from discharge from the hospital to about 2 months corrected age; from 70–100 kcal/kg/day of infant formula from 2 to 6 months corrected age; and 50–80 kcal/kg/day of infant formula from 6 to 12 months corrected age. At this consumption level, subjects randomized to receive the Control formula would ingest no DHA or ARA; those randomized to the DAS or DAF formulas would ingest 18.7–25.5 mg/kg/day of DHA from DHASCO®, the Martek single cell oil (DAS), or from the tuna fish oil (DAF), respectively, and 37.4–51.0 mg/kg/day of ARA (DAS and DAF) from ARASCO®, the Martek single cell oil, during hospitalization. The daily intake levels of DHASCO®, fish (tuna) oil, and ARASCO® during hospitalization can also be calculated for the three formula groups at intake levels of 110–150 kcal/kg/day. Infants receiving the Control formula would ingest no DHASCO®, fish (tuna) oil, or ARASCO®. As approximately 40% of the content of DHASCO® oil is DHA, infants receiving DAS would ingest 47–64 mg/kg/day of DHASCO®. The DHA content of the fish (tuna) oil used in the DAF formula is about 25.5%. Thus, infants receiving the DAF formula would ingest 73–100 mg/kg/day of fish (tuna) oil. As about 40% of the content of ARASCO® is ARA, infants receiving either the DAS or DAF formula would ingest 94–128 mg/kg/day of ARASCO® at the recommended formula intake levels of 110–150 kcal/kg/day. The fat blends and fatty acid composition of the three study formulas for each of the three types of formula—preterm, discharge, and term, are depicted in Table 4, Table 5, and Table 6, respectively. Table 4 includes a final column depicting the fat blend and fatty acid composition of the marketed iron-fortified Enfamil® Premature Formula at the time of the study. Table 5 and Table 6 do not contain data on the fat blends and fatty acid compositions of the marketed EnfaCare® and Enfamil® with Iron at the time of the study because their fat blends and fatty acid compositions are similar to the respective discharge and term Control study formulas.

The study protocol recommended that a preterm subject be fed the preterm formula (24 kcal/30 mL) for a minimum of fourteen days. After that, it was suggested that infants be switched to the discharge formula (22 kcal/30 mL) near the time of hospital discharge (± one week) and then to the term formula (20 kcal/30 mL) by 53 Weeks PMA (three months corrected age). However, in all cases the protocol stipulated that the choice of which type (caloric strength) of formula to use should be made by the investigator in charge as "medically indicated" for each subject. It is theoretically possible that some infants could have received the preterm (24-calorie) formula for the entire study period. Likewise, some infants might have graduated directly from the preterm (24-calorie) formula to the term (20-calorie) formula. Throughout the study, the investigator determined the appropriate type of formula—preterm, discharge, or term, to feed each subject, based on the subject's needs.

TABLE 4

Fat Blends and Fatty Acid Composition (Percent by Weight) of the Preterm Study Formulas

| Formula Component | | Study Group* | | | Marketed EPF** |
|---|---|---|---|---|---|
| | | C | DAS | DAF | |
| Fat Blend | | | | | |
| MCT Oil | | 40.0 | 40.0 | 40.0 | 40.0 |
| Soy Oil | | 30.0 | 30.0 | 30.0 | 40.0 |
| High Oleic Sunflower Oil | | 30.0 | 27.4 | 26.8 | 0.0 |
| DHA Single Cell Oil (DHASCO) ® | | 0.0 | 0.87 | 0.0 | 0.0 |
| ARA Single Cell Oil (ARASCO) ® | | 0.0 | 1.74 | 1.74 | 0.0 |
| Fish (Tuna) Oil | | 0.0 | 0.0 | 1.5 | 0.0 |
| Coconut Oil | | 0.0 | 0.0 | 0.0 | 20.0 |
| Fatty Acid | | | | | |
| 6:0 | Caproic Acid | 0.40 | 0.40 | 0.40 | 0.50 |
| 8:0 | Caprylic Acid | 29.0 | 29.0 | 29.0 | 30.0 |
| 10:0 | Capric Acid | 10.8 | 10.8 | 10.8 | 12.0 |
| 12:0 | Lauric Acid | 0.19 | 0.23 | 0.19 | 9.4 |
| 14:0 | Myristic Acid | 0.03 | 0.20 | 0.10 | 3.6 |
| 16:0 | Palmitic Acid | 4.2 | 4.4 | 4.6 | 5.9 |
| 18:0 | Stearic Acid | 2.4 | 2.6 | 2.6 | 2.4 |
| 20:0 | Arachidic Acid | 0.10 | 0.11 | 0.11 | 0.0 |
| 22:0 | Behenic Acid | 0.29 | 0.30 | 0.29 | 0.0 |
| 16:1 | Palmitoleic Acid | 0.0 | 0.02 | 0.08 | 0.0 |
| 18:1n-9 | Oleic Acid | 32.0 | 30.0 | 29.0 | 11.2 |
| 18:2n-6 | Linoleic Acid | 18.7 | 18.6 | 18.6 | 22.0 |
| 18:3n-3 | Alpha-linolenic Acid | 2.4 | 2.4 | 2.4 | 3.1 |
| 20:4n-6 | Arachidonic Acid | 0.0 | 0.67 | 0.67 | 0.0 |
| 20:5n-3 | Eicosapentaenoic Acid | 0.0 | 0.0 | 0.10 | 0.0 |
| 22:6n-3 | Docosahexaenoic Acid | 0.0 | 0.33 | 0.33 | 0.0 |

Notes:
*C = Control formula without DHA or ARA; DAS = formula with DHA and ARA from single cell oils; DAF = formula with DHA from tuna fish oil and ARA from single cell oil.
**Iron-fortified Enfamil ® Premature Formula marketed at the time the study was conducted.

TABLE 5

Fat Blends and Fatty Acid Composition (Percent by Weight) of the Discharge Study Formulas

| Formula Component | | C‡ | DAS | DAF |
|---|---|---|---|---|
| Fat Blend | | | | |
| MCT Oil | | 20.0 | 20.0 | 20.0 |
| Soy Oil | | 30.0 | 30.0 | 30.0 |
| High Oleic Sunflower Oil | | 35.0 | 32.5 | 31.9 |
| AHD Single Cell Oil (DHASCO) ® | | 0.0 | 0.84 | 0.0 |
| ARA Single Cell Oil (ARASCO) ® | | 0.0 | 1.67 | 1.67 |
| Fish (Tuna) Oil | | 0.0 | 0.0 | 1.46 |
| Coconut Oil | | 15.0 | 15.0 | 15.0 |
| Fatty Acid | | | | |
| 6:0 | Caproic Acid | 0.27 | 0.27 | 0.27 |
| 8:0 | Caprylic Acid | 15.5 | 15.5 | 15.5 |
| 10:0 | Capric Acid | 6.3 | 6.3 | 6.3 |
| 12:0 | Lauric Acid | 7.0 | 7.1 | 7.0 |
| 14:0 | Myristic Acid | 2.7 | 2.9 | 2.8 |
| 16:0 | Palmitic Acid | 5.8 | 6.0 | 6.1 |
| 18:0 | Stearic Acid | 3.1 | 3.2 | 3.3 |
| 20:0 | Arachidic Acid | 0.12 | 0.13 | 0.12 |
| 22:0 | Behenic Acid | 0.34 | 0.35 | 0.34 |
| 16:1 | Palmitoleic Acid | 0.0 | 0.02 | 0.07 |
| 18:1n-9 | Oleic Acid | 37.0 | 35.0 | 35.0 |
| 18:2n-6 | Linoleic Acid | 19.5 | 19.4 | 19.4 |
| 18:3n-3 | Alpha-linolenic Acid | 2.4 | 2.4 | 2.4 |
| 20:4n-6 | Arachidonic Acid | 0.0 | 0.64 | 0.64 |
| 20:5n-3 | Eicosapentaenoic Acid | 0.0 | 0.9 | 0.10 |
| 22:6n-3 | Docosahexaenoic Acid | 0.0 | 0.32 | 0.32 |

Notes:
*C = Control formula without DHA or ARA; DAS = formula with DHA and ARA from single cell oils; DAF = formula with DHA from tuna fish oil and ARA from single cell oil.
‡Contains same fat blend as EnfaCare ® marketed at the time the study was conducted.

TABLE 6

Fat Blends and Fatty Acid Composition (Percent by Weight) of the Term Study Formulas

| Formula Component | | C‡ | DAS | DAF |
|---|---|---|---|---|
| Fat Blend | | | | |
| Palm Olein Oil | | 45.0 | 43.9 | 43.6 |
| So Oil | | 20.0 | 19.5 | 19.4 |
| High Oleic Sunflower Oil | | 15.0 | 14.63 | 14.52 |
| DHA Single Cell Oil (DHASCO) ® | | 0.6 | 0.82 | 0.0 |
| ARA Single Cell Oil (ARASCO) ® | | 0.0 | 1.65 | 1.65 |
| Fish Tuna Oil | | 0.0 | 0.0 | 1.43 |
| Coconut Oil | | 20.0 | 19.5 | 19.4 |
| Fatty Acid | | | | |
| 6:0 | Caproic Acid | 0.10 | 0.11 | 0.10 |
| 8:0 | Caprylic Acid | 1.60 | 1.56 | 1.55 |
| 10:0 | Capric Acid | 1.20 | 1.18 | 1.17 |
| 12:0 | Lauric Acid | 9.3 | 9.1 | 9.0 |
| 14:0 | Myristic Acid | 4.1 | 4.1 | 4.0 |
| 16:0 | Palmitic Acid | 22.0 | 22.0 | 22.0 |
| 18:0 | Stearic Acid | 4.0 | 4.1 | 4.2 |
| 20:0 | Arachidic Acid | 0.23 | 0.24 | 0.24 |
| 22:0 | Behenic Acid | 0.19 | 0.22 | 0.22 |
| 16:1 | Palmitoleic Acid | 0.09 | 0.10 | 0.16 |
| 18:1n-9 | Oleic Acid | 38.0 | 37.0 | 37.0 |
| 18:2n-6 | Linoleic Acid | 17.5 | 17.2 | 17.1 |
| 18:3n-3 | Alpha-linolenic Acid | 1.68 | 1.65 | 1.65 |
| 20:4n-6 | Arachidonic Acid | 0.0 | 0.64 | 0.64 |
| 20:5n-3 | Eicosapentaenoic Acid | 0.0 | 0.0 | 0.10 |
| 22:6n-3 | Docosahexaenoic Acid | 0.0 | 0.32 | 0.32 |

Notes:
*C = Control formula without DHA or ARA; DAS = formula with DHA and ARA from single cell oils; DAF = formula with DHA from tuna fish oil and ARA from single cell oil.
‡Contains same fat blend as Enfamil ® with Iron, marketed at the time the study was conducted.

Term infants, who were expected to receive human milk almost exclusively (at least 80% of their intake—supplemented with no more than an average of six ounces/day of infant formula) until four months of age, were also enrolled in this study as a reference group. After four months of age, these term infants could receive breast milk or a marketed infant formula or a combination of the two until one year of age.

Overall Design and Plan of Study

The study was a two-phase (Phase I and Phase II), prospective, double-blind, randomized, controlled, parallel group trial conducted at seventeen pediatric centers in North America and Australia. Subject enrollment occurred from Oct. 17, 1997 to Aug. 21, 2000.

The overall plan of this study was to enroll premature infants within ten days of starting enteral feeding and after they had completed their first day of nutritive feeding, defined as any enteral feed >30 mL/kg/d. This enteral feed could be human milk; however, preterm infants initially fed human milk could only be enrolled into the study if supplementation with formula was necessary within ten days of the first nutritive human milk feeding. They were to be randomized to one of the three study formula groups. Premature subjects would ingest the study formula as the sole source of nourishment through Week 57 PMA, after which time juices and solids could be added to their diet. These subjects were to remain on their study formula through Week 92 PMA (one year corrected age). Normal term infants, who were to be breast-fed to four months of age, were to be enrolled into the study by one month of age and were to serve as a reference group. After four months of age, the term infants were expected to receive breast milk or a marketed infant formula until one year of age.

The study itself was divided into two phases. Only premature subjects could enroll in Phase I that extended from enrollment into the study until the subjects were 40 Weeks PMA. It included the hospitalization period for these preterm infants. Specific criteria were established to determine which preterm subjects could continue into Phase II of the study. For these infants, the Week 40 PMA study visit represented the completion of Phase I and enrollment into Phase II of the study. Term infants, who served as a reference group, only participated in Phase II of the study.

Phase I Synopsis

Parents of premature infants, whose birth weight was less than or equal to 1500 grams, whose gestational age was less than or equal to 35 Weeks PMA, and who had been on enteral feeds for less than ten total days (240 hours) after completing the first day of nutritive feeding (>30 mL/kg/d) with either human milk or formula were contacted and the study was explained to them. A written informed consent for study participation was obtained from parents who wished to enroll their infant in the study. Subjects were stratified by birth weight and gender and then randomized to one of three study formula groups: Control, DAS, or DAF. Information concerning the subject's birth date, weight, length, head circumference, gestational age, gender, and birth type (singleton, twin, etc.) was collected and recorded at enrollment. Information concerning the mother's obstetric history and reason for this preterm delivery was also documented. In addition, parental demographics, including data on the highest educational level the parents had achieved, were recorded. The daily exposure of the subject to cigarette smoking and the mother's eligibility for government subsidized income were also documented.

While in the hospital, the subjects were observed on a daily basis for enteral intake, the amount of residuals, stool frequency and characteristics, abdominal distention, and any utilization of IV lipids. Weekly, anthropometric measurements of the subject's weight, length, and head circumference were obtained. Infants were monitored for necrotizing enterocolitis (NEC); sepsis; bronchopulmonary dysplasia (BPD) and the need for respiratory support; retinopathy of prematurity (ROP); intraventricular hemorrhage (IVH); hydrocephaly; concomitant diagnoses; serious adverse events (SAE's); the use of antibiotics and glucocorticoids, and the administration of packed red blood cells.

After hospital discharge and until the 40 Week PMA Visit, any reports of adverse events were documented. At the 40 Week PMA Visit, anthropometrics were collected as were data on formula intake and acceptance and tolerance. At this final Phase I Visit, subjects were evaluated as to eligibility for enrollment in Phase II of the study.

Phase II Synopsis

Preterm subjects who successfully completed Phase I of the study were qualified to enter Phase II, if after enrollment, the study formula provided at least 80% of their enteral intake during hospitalization, and if at the 40 Week PMA Visit, the study formula provided 100% of their daily caloric intake. Phase II requirements of the study were discussed with the parents of these eligible subjects and if they chose to continue their infant in the study, informed consent was obtained.

To provide a reference standard, a group of healthy, term, breast-fed infants were included in Phase II of the study. Parents of healthy, appropriate for gestational age (AGA), singleton birth, term infants (38–42 weeks gestational age), who expected to nearly exclusively breast-feed their infants for four months, were contacted, the study explained to them, and informed consent obtained. These subjects were enrolled between birth and four weeks of age. Anthropometric birth data were recorded as were data on the mother's obstetric history, parental demographics, highest educational level attained by the parents, daily exposure of the study subject to smoking, and eligibility of the mother for government subsidized programs.

In Phase II, subjects made study visits at 44, 48, 53, 57, 66, 79, 92, and 118 Weeks PMA. Anthropometric data were collected at these visits, as were data on whether the subject had seen a doctor since the previous visit because they weren't well and whether they had regular contact with other children at home or in day care. At the 44 Week through 57 Week PMA Visits, information on compliance with the study feeding regimen, and a recall of the amount of study feeding (ounces of study formula for preterm subjects, number of breast feedings for the term subjects), stool frequency and stool characteristics, as well as tolerance data (excessive fussiness or gas) for the previous twenty-four hours were obtained. At the 57 Week PMA Visit, a blood sample was drawn from all preterm subjects. At this same time point, parents of preterm subjects were asked to complete a product evaluation questionnaire. At the 118 Week PMA Visit, mental and psychomotor development were evaluated by the Bayley Scales of Infant Development II and a final evaluation of the subject's participation in the study was made. Throughout Phase II, all subjects were monitored for the occurrence of adverse events and the use of antibiotics. Repeated efforts were made to follow-up on any preterm subject who discontinued before 40 Weeks PMA in Phase I or before 92 Weeks PMA in Phase II of the study.

Study Population

As the intent was to study the effects of the long-term feeding of infant formulas supplemented with LCPUFA in the general population of preterm infants, minimal eligibility criteria were used to restrict entry into the study. As per the revised protocol, premature subjects who were receiving enteral feeds, had a birth weight≦1500 grams and a gestational age≦35 Weeks PMA were acceptable subjects for this study if they had experienced less than ten total days (240 hours) of enteral feeds after completing the first day of nutritive feeding (>30 mL/kg/d) with either human milk or formula. Infants initially fed human milk could not be randomized into the study unless supplementation with formula was necessary within ten days after completing the first day of nutritive human milk feeding. Healthy, AGA term infants (38–42 weeks gestational age) who were of singleton birth and whose mothers anticipated breast feeding for at least four months were eligible to enroll in Phase II of this study.

Subjects were excluded from enrolling into this study if they had a history of underlying disease or congenital malformation which in the opinion of the investigator was likely to interfere with the evaluation of the subject. They were also excluded if they had any of the following diseases: gastroschisis, meconium ileus, obstruction, T.E. fistula, hepatitis, malrotation, abscesses, cystic fibrosis, Hirschsprung's disease, intussusception, biliary atresia, diaphragmatic hernia, ascites, or confirmed necrotizing enterocolitis (NEC) prior to enrollment. All prescription and over-the-counter medications, including vitamins, were allowed throughout both phases of the study.

Assignment to Formula Groups

Premature subjects who had experienced less than ten total days (240 hours) of enteral feeds after completing the first day of nutritive feeding (>30 mL/kg/d) with either formula or human milk were eligible for entry into the study provided that those whose first nutritive feeding was human milk had required supplementation with infant formula within ten days of the first feeding. Eligible preterm infants were stratified by gender and birth weight and randomized into one of three study formula groups: Control, DAS, or DAF. Separate randomization schedules were prepared for males and females in each of the weight categories to accommodate these stratification factors.

Randomization of study infants at each clinical site was accomplished in the following manner. The sponsor supplied each investigative site with six sets of sealed envelopes containing product codes. After elimination from the study of the>1500 grams weight category, only four sets of sealed envelopes were used. The sets were designated for 1) males with a birth weight<1000 grams, 2) males with a birth weight between 1000 and 1500 grams, 3) females with a birth weight <1000 grams, and 4) females with a birth weight between 1000 and 1500 grams. When a preterm infant was eligible for enrollment into the study, the Investigator retrieved the next envelope in sequence from the appropriate set, based on the gender and birth weight of the subject. The sealed envelope was then opened to reveal the product code of the formula that the subject would receive. The infant's initials, birth date, and informed consent date were then recorded on the randomization sheet, which was retained at the investigative site. The envelope randomization procedure was used to reduce bias at the study site.

Instructions for Formula Use

Three types of study formula (preterm, discharge, and term) were provided for each study formula group. Thus, for each study formula group, there were three caloric strengths: 24, 22, and 20 kcal/30 mL. The premature formula (24 kcal/30 mL), was packaged in a three fluid ounce nursette with forty-eight nursettes per case. The preterm discharge formula (22 kcal/30 mL) was packaged in eight fluid ounce cans with twelve cans per case. The term formula (20 kcal/30 mL) was packaged in thirty-two fluid ounce cans with six cans per case. The preterm, discharge, and term formulas for each study formula group were supplied in ready-to-use form. During hospitalization, nursery personnel recorded for each subject, during each twenty-four hour period, the amount of formula ingested, the amount of expressed human milk ingested, the addition of any human milk fortifier to the feeds, the number of feeds given from the breast, and the amount of residuals measured. Upon discharge, parents fed their infants at home. Unless otherwise instructed by their physician, they were told to use the study formula as the sole source of nutrition through the 57 Week PMA Visit. After that, they could feed cereals or other solids, and juices. They were instructed to continue using the study formula up to the 92 Week PMA Visit (one year corrected age). The amount of each feeding and the frequency of feedings were left up to the discretion of the parents. At the 40, 44, 48, 53, and 57 Week PMA Study Visits, site personnel asked parents to recall how much study formula their infant had ingested in the previous twenty-four hours.

Blinding

The sponsor's (Mead Johnson & Company) personnel, the Investigator, all study site personnel, and the parents/care givers of the subjects were blinded to the identity of the study product. Each study product was divided into two sub-batches and a randomly generated product code was assigned to each of the sub-batches. Each can or product was labeled with a plain paper clinical label that contained the product code and information on use. The labels were color-coded by product code to assist the Investigator in dispensing the appropriate product, according to the randomization schedule, to each subject. Cases were labeled in a similar fashion. All study site personnel remained blinded throughout the study. Except for the statistician, the blind was not broken for Mead Johnson personnel until the issuance of the draft version of the Final Study Report.

Data Collection and Study Methods in Phase I Enrollment

At the time of enrollment and randomization, the Investigator or his/her designee recorded the birth date, gender, race, birth weight, length, head circumference, postmenstrual age at birth, and birth type (singleton, twin, triplet, quadruplet or other) of the subject. He/she also verified that the subject met the study criteria and that written informed consent had been obtained from the parent/guardian. Anthropometric measurements of the study infant were then obtained. In addition, the maternal obstetric history, parental demographic data, as well as information on the highest educational level obtained by the parents were recorded. Information on the daily exposure of the subject to cigarette smoking, and the eligibility status of the mother for government subsidized income were also documented.

Special Parameters

Because preterm infants often have concomitant medical conditions that affect their overall health, it was important to track these conditions in the preterm subjects in this study. In Phase I, during the hospitalization period, the occurrence of any diagnosed concomitant medical conditions, necrotizing enterocolitis (NEC), sepsis, retinopathy of prematurity (ROP), intraventricular hemorrhage (IVH), and bronchopulmonary dysplasia (BPD) were recorded. In addition, any required respiratory support, antibiotics, blood transfusions, or IV lipid administration were documented. Specific forms were provided to the sites for recording these data.

Adverse Events

After discharge from the hospital, the preterm subjects were monitored throughout Phase I for the occurrence of adverse events. The investigator was required to note the date of the event, its severity, relationship to study product, and clinical outcome.

Serious Adverse Events

Serious Adverse Events, defined as those that result in a life-threatening event or death; require or prolong hospitalization; result from an overdose; or result in permanent disability, were documented by the investigator. Sites were required to report serious adverse events immediately to the sponsor and to notify the Institutional Review Board of the event, regardless of whether it was product-related.

Data Collection and Study Methods in Phase II Enrollment

Preterm subjects who completed Phase I of the study were eligible to enter Phase II the study formula had provided at least 80% of their enteral intake during the hospitalization period of Phase I and if, at Week 40 PMA, it provided 100% of their dairy caloric intake. The enrollment data collected at entry into Phase I of the study served as the enrollment data for Phase II for those preterm subjects who continued into Phase II of the study.

For the term subjects, the Investigator or his/her designee recorded the birth date, gender, race, birth weight, length, and head circumference. He/she also verified that the subject met the study criteria and that written informed consent had been obtained from the parent/care giver. In addition, information on maternal obstetric history; parental demographics, and highest education level obtained; daily exposure of the infant to cigarette smoking; and the eligibility status of the mother for government subsidized income were also obtained.

Diagnoses During Hospitalization

Any medical conditions diagnosed for a subject during the hospitalization period were recorded. For studies in the United States, the diagnoses were coded on the hospital discharge records, using ICD-9-CM codes (U.S. Department of Health and Human Services, 1999). For studies outside the United States, the diagnoses were coded using the same ICD-9-CM codes by clinical research personnel at the sponsor's site. The types of diagnoses for which ICD-9-CM codes are available are diseases, external causes of injuries, and procedures.

Results

Phase I 361 (119 C, 112 DAS, 130 DAF) subjects enrolled in Phase I of the study and received study formula. Two (1 C, 1 DAS) subjects were removed from the study by the sponsor; 305 (98 [83%] C, 95 [86%] DAS, 112 [86%] DAF) subjects completed Phase I. There were no statistically significant differences (p=0.806) among the study formula groups for discontinuation from Phase I, or for the percentage of days subjects received glucocorticoid therapy. There were no statistically significant differences in the rate of growth or achieved growth at 40 Weeks PMA for weight, length, or head circumference among the study formula groups.

During hospitalization, mean caloric intake of study formula, mean total enteral caloric intake, daily residuals, stool frequencies, stool consistency, and the presence of abdominal distention were similar among groups. Analyses of the 24-hour parental recall data for the day prior to the 40 Weeks PMA Study Visit showed subjects in the DAF group had been reported to have ingested significantly less study formula than subjects in the DAS group (p=0.003). All groups had similar stool frequencies and stool consistencies, but Control subjects had fewer brown and more yellow stools than subjects in the supplemented groups (p=0.048). Fussiness, diarrhea, and constipation were similar among the 3 study groups at 40 Weeks PMA.

The frequency of concomitant illnesses were similar for 178 of 180 diagnostic categories among the 3 study formula groups. More Control (11 [9%]) than DAF (0 [0%]) subjects were diagnosed with "Other Conditions of the Brain." More DAS (5 [4%]) than DAF (0 [0%]) subjects were diagnosed with "Nonspecific Low Blood Pressure Readings." There were no differences among the groups in adverse events or serious adverse events. There were 5 deaths (2 C, 3 DAF) in Phase I. One Control and 1 DAF subject succumbed to necrotizing enterocolitis (NEC) and sepsis, 2 (1 C, 1 DAF) subjects died of pneumonia, and 1 DAF subject died from sepsis. There were no statistically significant differences among the study groups in the occurrence of NEC or any stage of NEC, sepsis or suspected sepsis, retinopathy of prematurity (ROP), the use of laser or cryoretinal therapy for ROP, bronchopulmonary dysplasia, or the need for respiratory support.

Intraventricular hemorrhage (IVH) did occur significantly fewer times in DAS subjects (14 [13%]) than in Control (32 [29%]) or DAF (33 [27%]) subjects. The 3 groups were comparable in regards to the number of subjects with no IVH or Stage 1 or Stage 2 IVH versus the number with Stage 3 or Stage 4 IVH. There were no differences among the groups in regards to the low number of subjects with posthemorrhagic hydrocephalus (2 [2%]) C, 1 [1%] DAS, 2 [2%] DAF). Follow-up information was available for 35 of the 54 subjects who discontinued early from Phase I of the study.

Phase II 105 term and 245 preterm subjects entered Phase II. 2 term and 7 (3 C, 2 DAS, 2 DAF) preterm subjects were removed from the study by the sponsor. Of the remaining 103 term subjects and 238 (80 C, 70 DAS, 88 DAF) preterm subjects who entered Phase II, 76 (74%) term subjects and 179 (62 [78%] C, 52 [74%] DAS, 65 [74%] DAF) preterm subjects completed the study.

There were no statistically significant differences among the groups in the discontinuation rate. From 66 through 118 Weeks PMA, the DAS group had a significantly greater mean achieved weight than the Control group and at 118 Weeks PMA, it was also significantly greater than that for the DAF group. The term HM group had a significantly greater mean weight than the C, DAS, or DAF groups from 40 through 92 Weeks PMA. At 118 Weeks PMA, the mean weight of the term HM group was still significantly greater than that for the C or DAF group, but not for that of the DAS group. The mean achieved length of the DAS group was significantly greater than that of the Control group at 48, 79, and 92 Weeks PMA. The mean length of the term HM group was significantly greater than the C, DAS, and DAF groups from 40 through 66 Weeks PMA and from then on it only was greater than the C and DAF groups, and not different from the DAS group.

There were no statistically significant differences throughout Phase II between the DAS and Control groups in mean head circumference; they were comparable among all 4 study groups through 66 Weeks PMA; the small differences noted from 79 to 118 Weeks PMA between the human milk group and the Control and/or DAF group were not clinically significant. Subjects in all study formula groups demonstrated comparable good acceptance and tolerance of the study formulas. In general, analysis of the 24-hour parental recall data showed the groups were comparable in regards to stool frequency, consistency and color, and a low occurrence of diarrhea, constipation, and fussiness.

Term subjects had higher Bayley Scales of Infant Development II scores for mental and psychomotor development than preterm subjects. DAS and DAF subjects had significantly or marginally higher mental and psychomotor developmental scores than Control subjects as shown below. Results of laboratory studies done on blood drawn at 57 Weeks PMA from preterm infants showed no differences among the 3 study formula groups except that the DAF group had a lower potassium value and a higher mean corpuscular hemoglobin value than the Control group and a higher total cholesterol value than either the Control or DAS group. None of these differences were of clinical significance. Reports of adverse events were similar among the study groups. Subjects in the Control group had significantly more events reported for the nervous system than did the DAF group. The deaths of 2 Control subjects were reported in Phase II, both attributed to SIDS. The incidence of adverse events related or possibly related to study product was small ($\leq 4\%$); the majority of such events occurred in the "Gastrointestinal" body system. Too few visual acuity data were collected for analysis.

Conclusions

It is safe to feed premature, discharge, and term formulas supplemented with DHA, sourced from the single cell oil DHASCO® or tuna fish oil and ARA sourced from the single cell oil ARASCO®, at the median levels found in human milk to VLBW preterm infants, even those with significant morbidity. These formulas may be fed as the sole source of calories until 57 Weeks PMA and as the main source of calories until 92 Weeks PMA without increased risk for diseases associated with prematurity, sepsis, adverse events, or abnormal laboratory measurements. Compared to an unsupplemented formula, feeding preterm infants formulas supplemented with DHA and ARA from single cell oils may provide long-term growth benefits and feeding formulas supplemented with DHA from single cell or fish oils and ARA from single cell oil may improve mental and psychomotor development at 118 Weeks PMA.

Results regarding Intraventricular Hemorrhage (IVH)

During hospitalization, results for all ultrasound studies done to diagnose intraventricular hemorrhage (IVH) were recorded. The results of these studies are summarized in Table 7. Subjects were classified by the maximum grade of IVH detected on either side of the head.

TABLE 7

Intraventricular Hemorrhage (IVH)

| | | Study Group* | | |
|---|---|---|---|---|
| | | C | DAS | DAF |
| Ultrasound for IVH | Not Done | 7 | 3 | 7 |
| Maximum Grade Detected | None | 80 | 95 | 90 |
| | I | 20 | 8 | 21 |
| | II | 8 | 3 | 6 |
| | III | 1 | 2 | 3 |
| | IV | 3 | 1 | 3 |

*C = Control formula; DAS = formula with DHA and ARA from single cell oils, DAF = formula with DHA from tuna fish oil and ARA from single cell oil.

Ultrasonography to detect intraventricular hemorrhage was not performed in seventeen (7 C, 3 DAS, 7 DAF) subjects. Of the three hundred forty-four (112 C, 109 DAS, 123 DAF) subjects who underwent ultrasonography to detect IVH, two hundred sixty-five (80 C, 95 DAS, 90 DAF) subjects had no IVH detected. Grade I was the maximum grade of IVH detected for forty-nine (20 C, 8 DAS, 21 DAF) subjects while Grade II was the maximum grade detected for seventeen (8 C, 3 DAS, 6 DAF) subjects. Only six (1 C, 2 DAS, 3 DAF) subjects demonstrated Grade Iii IVH while seven (3 C, 1 DAS, 3 DAF) subjects showed Grade IV IVH.

A statistical analysis was conducted to compare the number of subjects in each study group who had no IVH to those who had any grade of IVH. A second statistical analysis to compare the number of subjects in each group who had no IVH or Grade I or II IVH, to those who had Grade III or IV IVH was conducted. In addition, a third statistical comparison of the number of subjects in each group who developed post-hemorrhagic hydrocephalus was also done. The results of these analyses are shown in Table 8. For the second analysis, subjects who had not had an ultrasound were included as having "No IVH or Grade I or II IVH" because in the Medical Director's opinion, if a subject had experienced symptoms severe enough to be categorized as a Grade III or IV IVH, they would most likely have had an ultrasound study or been diagnosed as having IVH. It was possible an infant with a Grade I or II IVH might not have demonstrated symptoms severe enough to require an ultrasound study. Therefore, subjects without an ultrasound were included in this analysis as having "No IVH or Grade I or Grade II."

TABLE 8

Occurrence of Intraventricular Hemorrhagic and Posthemorrhagic Hydrocephalus

| | Study Group* | | |
|---|---|---|---|
| | C | DAS | DAF |
| No IVH Detected | 80 | 95 | 90 |
| IVH Present | 32 | 14 | 33 |
| No IVH or Grade I or II | 115 | 109 | 124 |
| Grade III or IV IVH | 4 | 3 | 6 |
| No Posthemorrhagic Hydrocephalus | 116 | 111 | 127 |
| Posthemorrhagic Hydrocephalus | 2 | 1 | 2 |

*C = Control formula; DAS = formula with DHA and ARA from single cell oils; DAF = formula with DHA from tuna fish oil and ARA from single cell oil.

Ultrasound studies performed on three hundred forty four (112 C, 109 DAS, 123 DAF) subjects detected the presence of intraventricular hemorrhage in thirty-two (29%) of the Control subjects, fourteen (13%) of the DAS subjects, and thirty-three (27%) of the DAF subjects. There were statistically significantly more subjects in the Control group (p=0.005) and in the DAF group (p=0.009) for whom any stage of IVH was detected than there were in the DAS group. There was no statistically significant difference (p=0.773) in the detection of IVH by ultrasound between subjects in the Control and DAF study formula groups.

Regarding development of Grade III and IV, there was no statistically significant difference among groups. For this analysis, subjects for whom no ultrasound studies had been performed were included in the "no IVH or Grade I or II IVH" group. When this group was compared to those with Grade III or IV IVH, no statistically significant differences (p=0.776) were among the formula groups. Grade III or IV IVH was detected in 5% or less of the subjects in any formula group. The development of posthemorrhagic hydrocephalus occurred in only two (2%), one (1%), and two (2%) of the Control, DAS, and DAF subjects, respectively. There were no statistically significant differences (p=1.00) among the study formula groups in regard to the development of posthemorrhagic hydrocephalus.

Because the results from all ultrasound studies done to diagnose IVH were collected during hospitalization, it was possible that many of the ultrasounds were done early in an infant's life, prior to enrollment into the study. Thus, it is possible that the most severe grade of IVH detected for a given subject might have occurred prior to that infant starting on study formula. Therefore, a second set of analyses were done to determine how many subjects had ultrasounds done prior to enrollment into the study and of these, what the maximum grade of IVH detected was. Table 9 depicts the maximum grade of IVH detected for subjects who underwent ultrasonography to diagnose IVH prior to the study enrollment.

TABLE 9

Intraventricular Hemorrhage Before Study Enrollment

| | | Study Group* | | |
|---|---|---|---|---|
| | | C | DAS | DAF |
| Maximum Grade Detected | None | 67 | 75 | 83 |
| | I | 10 | 3 | 10 |
| | II | 4 | 3 | 5 |
| | III | 0 | 1 | 3 |
| | IV | 3 | 1 | 3 |

*C = Control formula; DAS = formula with DHA and ARA from single cell oils; DAF = formula with DHA from tuna fish oil and ARA from single cell oil.

As is evident from comparing the above table to Table 7, eighty-four of the 112 Control subjects, eighty-three of the 109 DAS subjects, and one hundred four of the one hundred twenty-three DAF subjects did undergo an ultrasound study to detect IVH prior to enrollment into the study. All seven (3 C, 1 DAS, 3 DAF) subjects who demonstrated a Grade 4 IVH were diagnosed with this grade of IVH prior to enrollment into the study. Likewise, of the six total subjects with a Grade 3 IVH reported in Table 7, four (1 DAS, 3 DAF) subjects were found to have had this degree of IVH prior to enrollment into the study.

A statistical analysis of the IVH data collected prior to study enrollment was also undertaken. Statistical analyses were conducted to compare the number of subjects in each study group who had no IVH to those who had any grade of IVH and to compare the number of subjects in each group who had no IVH or Stage 1 or 2 IVH to those who had Stages 3 or 4 IVH.

Subjects for whom ultrasounds had not been performed were included in the second analysis as described before. The results of these analyses are shown in Table 10.

TABLE 10

Occurrence of Intraventricular Hemorrhage Before Study Enrollment

| | Study Group* | | |
|---|---|---|---|
| | C | DAS | DAS |
| No IVH Detected | 67 | 75 | 83 |
| IVH Present | 17 | 8 | 21 |
| No IVH or Grade I–II | 116 | 110 | 124 |
| Grade III–IV IVH | 3 | 2 | 6 |

*C = Control formula; DAS = formula with DHA and ARA from single cell oils; DAF = formula with DHA from tuna fish oil and ARA from single cell oil.

For study subjects who were diagnosed with IVH prior to enrolling into the study, there were no statistically significant differences (p=0.096) among the study formula groups in regards to the number of subjects with no IVH detected compared to those with some grade of IVH present. Likewise, there were no statistically significant differences (p=0.473) among the study formula groups in regards to the number of subjects with no IVH or Grade I or II IVH compared to those with a Grade III or IV IVH. Of the five (2 C, 1 DAS, 2 DAF) subjects who were shown in Table 53 as having developed posthemorrhagic hydrocephalus, four (1 C, 1 DAS, 2 DAF) developed posthemorrhagic hydrocephalus prior to study enrollment. Only one Control subject developed this condition after enrolling.

From Table 7 and Table 10, it can be seen that 33 IVH cases (all grades) were detected for the first time after enrollment (15 C, 6 DAS and 12 DAF), as shown in Table 11. A two-sided Fisher's Exact Test indicates a statistically significant difference (p=0.036) between the Control and DAS formula groups. The DAF group was not statistically different from the Control formula group (p=0.53).

TABLE 11

IVH Cases Detected For The First Time After Study Enrollment

| | Study Group* | | |
|---|---|---|---|
| | C | DAS | DAF |
| No IVH detected | 80 | 95 | 90 |
| IVH detected after enrollment | 15 | 6 | 12 |

*C = Control formula; DAS = formula with DHA and ARA from single cell oils; DAF = formula with DHA from tuna fish oil and ARA from single cell oil.

Finally, evidence suggest that, in adults, administration of n-3 LCPUFA has a beneficial effect on high blood pressure. See Mori, T. A. et al., Hypertension 1999; 34:253–260. There may also be a correlation between neonatal LCPUFA intake and low blood pressure. Several studies indicate that breast-fed infants have lower blood pressure later in life than their formula-fed cohorts. See Wilson, A. C. et al., Brit Med J 1998; 316:21–25; see also Taittonen, L. et al., Ped Res 1996; 40:627–632. These findings suggest that the presence of LCPUFA in breast milk may contribute to an advantageous lowering of blood pressure during adult life.

All references cited in this specification, including without limitation all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by the authors and no admission is made that any reference constitutes prior art. Applicants reserve the right to challenge the accuracy and pertinency of the cited references.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. A method to reduce the incidence of Intraventricular Hemorrhage in newborn infants, the method comprising administering to those infants an effective amount of DHA and ARA from a source that is substantially free of EPA.

2. The method of claim 1 wherein the source of DHA and ARA is single cell oils.

3. The method of claim 1 wherein DHA and ARA are supplemented into infant formulas.

4. The method of claim 1 wherein the ratio of ARA:DHA is from about 1:3 to about 9:1.

5. The method of claim 1 wherein the ratio of ARA:DHA is from about 1:2 to about 4:1.

6. The method of claim 1 wherein the ratio of ARA:DHA is from about 2:3 to about 2:1.

7. The method of claim 1 wherein the ratio of ARA:DHA is about 2:1.

8. The method of claim 1 wherein the amount of DHA administered to the infant is from about 3 mg to about 150 mg per kg of the infant's body weight per day.

9. The method of claim 1 wherein the amount of DHA administered to the infant is from about 6 mg to about 100 mg per kg of the infant's body weight per day.

10. The method of claim 1 wherein the amount of DHA administered to the infant is from about 10 mg to about 60 mg per kg of the infant's body weight per day.

11. The method of claim 1 wherein the amount of DHA administered to the infant is from about 15 mg to about 45 mg per kg of the infant's body weight per day.

12. The method of claim 1 wherein the amount of DHA administered to the infant is from about 15 mg to about 30 mg per kg of the infant's body weight per day.

13. The method of claim 3 wherein the source of DHA and ARA is single cell oils.

14. The method of claim 3 wherein the infant formula comprises DHA in an amount of about 5 mg/100 kcal to about 80 mg/100 kcal and ARA in an amount of about 10 mg/100 kcal to about 100 mg/100 kcal.

15. The method of claim 3 wherein the infant formula comprises DHA in an amount of about 10 mg/100 kcal to about 50 mg/100 kcal and ARA in an amount of about 15 mg/100 kcal to about 70 mg/100 kcal.

16. The method of claim 3 wherein the infant formula comprises DHA in an amount of about 15 mg/100 kcal to about 20 mg/100 kcal and ARA in an amount of about 20 mg/100 kcal to about 40 mg/100 kcal.

17. A method for reducing the incidence of Intraventricular Hemorrhage in newborn infants, the method comprising feeding the infants after weaning with a formula comprising fats, proteins, carbohydrates, and an effective amount of ARA and DHA from a source substantially free of EPA.

18. The method of claim 17 wherein the source of DHA and ARA is single cell oils.

19. The method of claim 17 wherein the ratio of ARA:DHA is from about 1:3 to about 9:1.

20. The method of claim 17 wherein the ratio of ARA:DHA is from about 1:2 to about 4:1.

21. The method of claim 17 wherein the ratio of ARA:DHA is from about 2:3 to about 2:1.

22. The method of claim 17 wherein the ratio of ARA:DHA is about 2:1.

23. The method of claim 17 wherein the amount of DHA administered to the infant is from about 3 mg to about 150 mg per kg of the infant's body weight per day.

24. The method of claim 17 wherein the amount of DHA administered to the infant is from about 6 mg to about 100 mg per kg of the infant's body weight per day.

25. The method of claim 17 wherein the amount of DHA administered to the infant is from about 10 mg to about 60 mg per kg of the infant's body weight per day.

26. The method of claim 17 wherein the amount of DHA administered to the infant is from about 15 mg to about 45 mg per kg of the infant's body weight per day.

27. The method of claim 17 wherein the amount of DHA administered to the infant is from about 15 mg to about 30 mg per kg of the infant's body weight per day.

28. The method of claim 17 wherein DHA and ARA from a source substantially free of EPA are supplemented into infant formulas.

29. A method to control and prevent high blood pressure in an adult subject by administering to said adult subject while the subject is an infant, an effective blood pressure-reducing amount of DHA and ARA from a source that is substantially free of EPA.

* * * * *

UNITED STATES PATENT AND TRADEMARK OFFICE
CERTIFICATE OF CORRECTION

PATENT NO.   : 6,753,350 B1
DATED        : June 22, 2004
INVENTOR(S)  : James W. Hansen, Karen H. Knauff and Deborah A. Schade It is certified that error appears in the above-identified patent and that said Letters Patent is hereby corrected as shown below:

Title page,
Item [56], References Cited, OTHER PUBLICATIONS,
"Abstract of article published in British Medical Journal" reference, replace the term "Abstracts" with the term -- Abstract --.

Column 1,
Line 58, replace the term "computer" with the term -- computed --.

Column 4,
Line 9, after the term "not" delete ",".

Column 13,
Table 5, 4th entry under "Fat Blend", replace the term "AHD" with the term -- DHA --.
Table 5, 15th entry under "Fatty Acid", replace the term "0.9" with the term -- 0.0 --.
Table 6, 2nd entry under "Fat Blend", replace the term "So" with the term -- Soy --.
Table 6, 1st entry under "Fatty Acid", replace the term "0.11" with the term -- 0.10 --.

Column 18,
Line 29, insert the term -- if -- between the terms "II" and "the".

Column 21,
Line 26, replace the term "IIi" with the term -- III --.
Line 66, replace the terms "forty four" with the term -- forty-four --.

Signed and Sealed this

First Day of February, 2005

JON W. DUDAS
*Director of the United States Patent and Trademark Office*